United States Patent [19]
Hunsicker et al.

[11] Patent Number: 6,130,343
[45] Date of Patent: *Oct. 10, 2000

[54] METHOD OF PRODUCING A TOCOPHEROL PRODUCT

[75] Inventors: Jeffrey C. Hunsicker, Naperville, Ill.; John F. Verhoeven, Ivens, Utah; F. Scott McCunn, Phoenix, Ariz.

[73] Assignee: Henkel Corporation, Gulph Mills, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/705,078

[22] Filed: Aug. 29, 1996

Related U.S. Application Data

[63] Continuation of application No. 08/430,213, Apr. 26, 1995, abandoned.

[51] Int. Cl.⁷ .................................................. C07D 311/72
[52] U.S. Cl. ............................................................. 549/410
[58] Field of Search ............................................. 549/410

[56] References Cited

U.S. PATENT DOCUMENTS

| | | | |
|---|---|---|---|
| 2,680,749 | 12/1954 | Cawley et al. | 260/345.5 |
| 3,538,119 | 11/1970 | Grant | 260/345.5 |
| 3,551,457 | 12/1970 | Ross | 260/345.5 |
| 3,608,083 | 9/1971 | Bunnell et al. | 424/284 |
| 3,655,852 | 4/1972 | Koff et al. | 264/115 |
| 3,914,430 | 10/1975 | Cannalonga et al. | 424/284 |
| 3,947,596 | 3/1976 | Cannalonga et al. | 424/344 |
| 3,962,384 | 6/1976 | Cannalonga et al. | 264/7 |
| 4,511,685 | 4/1985 | Nissen et al. | 524/110 |
| 4,617,292 | 10/1986 | Satoh et al. | 514/27 |
| 4,702,919 | 10/1987 | Kitamori et al. | 424/490 |
| 4,870,196 | 9/1989 | Thorengaard | 549/410 |
| 5,114,720 | 5/1992 | Littell et al. | 424/478 |
| 5,120,761 | 6/1992 | Finnan | 514/458 |
| 5,290,569 | 3/1994 | Nagafuzi et al. | 424/490 |
| 5,328,903 | 7/1994 | Ishii et al. | 514/168 |

FOREIGN PATENT DOCUMENTS

| | | |
|---|---|---|
| 866489 | 4/1961 | United Kingdom . |
| 1007161 | 10/1965 | United Kingdom . |
| 1114150 | 5/1968 | United Kingdom . |

OTHER PUBLICATIONS

C.E. Capes, "Size Enlargement," *Encyclopedia of Chemical Technology*, vol. 21, pp. 77–105, (Kirk–Othmer, eds., John Wiley and Sons, Inc., NY, NY 1983).

F. Zenz, "Fluidization", *Encyclopedia of Chemical Technology*, vol. 10, pp. 548–581 (Kirk–Othmer, eds., John Wiley and Sons, Inc., NY, NY, 1980).

E.K. Just and T.G. Majewicz, "Cellulose Ethers," *Encyclopedia of Polymer and Science Engineering*, vol. 3, pp. 226–269 (John Wiley and Sons, Inc., NY, NY 1985).

*Primary Examiner*—Amelia Owens
*Attorney, Agent, or Firm*—John E. Drach; Glenn E. Murphy; Daniel S. Ortiz

[57] ABSTRACT

A process of producing a coated tocopheryl succinate is provided. The process comprises contacting a tocopheryl succinate powder with a solution of a pharmaceutically acceptable binder, said tocopheryl succinate being maintained in a fluidized bed during said contacting by passage of a fluidizing gas through said bed. The solvent is then evaporated from said contacted tocopheryl succinate in said fluidized bed. The temperature of said fluidizing gas when introduced into said bed is sufficiently low, e.g. no higher than about 30° C., such that the bed of tocopheryl succinate remains in a fluidized state during said contacting and said evaporating.

35 Claims, No Drawings

METHOD OF PRODUCING A TOCOPHEROL PRODUCT

This application is a continuation of applicaiton Ser. No. 08/430,213 filed on Apr. 26, 1995 now abandoned.

FIELD OF THE INVENTION

The present invention relates to a method of producing by granulation a tocopheryl succinate having a desirable particle size.

BACKGROUND OF THE INVENTION

Tocopherol compounds, also designated as vitamin E, are active components in vegetable oils. Vitamin E activity refers to the physiological activity of this group of nutrient materials. Materials having a vitamin E activity all belong to a distinct series of compounds which are all derivatives of chroman-6-ol. These compounds are all tocol derivatives having an isoprenoid C16-sidechain. The term "tocol" is used to mean 2-methyl-2-(4', 8', 12'-trimethyltridecyl) chroman-6-0l. These compounds are alpha-, beta-, gamma-, and delta-tocopherol, and are of primary importance for vitamin E activity. Of these, alpha-tocopherol has the highest vitamin E activity and is the most valuable.

Such naturally occurring tocopherol homologues are generally isolated from natural products such as vegetable oil sources by various combinations of procedures such as esterification, saponification, extraction, distillation, ion exchange, adsorption chromatography, precipitation of sterols, and crystallization. The tocol concentrate isolated will vary depending on the particular separation technique used in addition to the vegetable source. One such concentrate, for example, contains mixtures of tocopherol with approximately 40% by weight residual sterols and hydrocarbons.

A well known commercial activity is the conversion of tocopherol, and especially d-alpha-tocopherol, into a solid form for convenient human consumption. One of the best methods commercially used to solidify tocopherol is to prepare tocopheryl succinate. Typically, tocopheryl succinate is prepared by reacting tocopherol with succinic anhydride, and then isolating the half ester product by crystallization. References describing methods of this nature are described in U.S. Pat. No. 3,538,119 and in British Patent No. 866,489. Another reference which describes both the preparation of alpha-tocopheryl succinate and its recovery is British Patent No. 1,114,150.

For medicinal and health applications requiring tocopherol, solid tocopherol derivatives are prepared. It is desired that such tocopherol derivatives be capable of dissolving in an aqueous solution and be highly potent with a high degree of vitamin E biological activity per unit. The preparation of tocopherol derivatives is described in U.S. Pat. No. 2,680,749, which describes, as a preferred method, reacting tocopherol with a suitable polybasic acid anhydride such as succinic acid anhydride under usual esterification conditions.

Tocopheryl succinate, which is a vitamin E, melts at about 73°–78° C. It is a white solid material which at room temperature is waxy and tacky and which has poor flow properties. Furthermore, the commercially available tocopheryl succinate ordinarily has a broad particle size distribution with many fine particles which causes the powder to be cohesive and to form lumps. Therefore, it is difficult to formulate it into capsules and tablets having an exact content of the active compound in the methods normally employed for the formulation of vitamin preparations.

A number of attempts have been made to prepare free-flowing tocopheryl succinate with and without additives. A prior art method is disclosed in U.S. Pat. No. 3,551,457. In this method tocopheryl succinate is heated to melt it, i.e., to about 85° C., and the melt is poured into a shallow pan so as to form a layer having a thickness of between 0.3 and 2.5 cm, after which the melt is allowed to harden and crystallize over a period of 12–24 hours. The resulting mass is then ground at a low temperature, preferably at a temperature of about −80° C. The prior art method is not suitable for commercial production because of the requirement of grinding at a very low temperature.

British Patent No. 1,007,161 discloses another method of preparing free-flowing, powdered tocopheryl succinate having a high bulk density. In the method tocopheryl succinate is melted and the melt is dispersed in an aqueous solution containing a thickening agent in the form of methyl cellulose, and subsequently the dispersion formed is quickly cooled so as to cause the tocopheryl succinate to crystallize to form fine particles which are separated and dried. A product thus prepared has a relatively broad particle size distribution which causes problems in the treatment of the product in known tabletting machines. Furthermore, the use of methyl cellulose as thickening agent results in a certain tackiness which imparts to the product a tendency to, adhere to e.g., parts of the tabletting machine.

U.S. Pat. No. 4,870,196 (Thorengaard) discloses a method of preparing powdered, free-flowing tocopheryl succinate having a high bulk density comprising melting a mixture of tocopheryl succinate and wax, spraying the melt in a spraying zone containing a cloud of a powdering agent consisting of fine tocopheryl succinate and an additional powdering agent, and maintaining the product formed in a fluidized state by introducing cooling air until the tocopheryl succinate particles have hardened, and separating the product formed into a product fraction and a fine fraction, and recycling the fine fraction to the spraying zone.

Thorengaard reports that attempts to prepare tocopheryl succinate in the form of particles coated with other agents that the ones described above have not produced satisfactory results as these attempts have resulted in the reduction of the tocopheryl succinate content of the final product. It is stated that this is undesirable because of the subsequent preparation of high-dosed capsules and tablets since for such use it is desirable that the starting material contains as much tocopheryl succinate as possible and that it also has a high bulk density.

SUMMARY OF THE INVENTION

This invention relates to a method of producing a coated tocopheryl succinate comprising:

contacting a tocopheryl succinate powder with a solution of a pharmaceutically acceptable binder, said tocopheryl succinate being maintained in a fluidized bed during said contacting by passage of a fluidizing gas through said bed, and evaporating solvent from said tocopheryl succinate in said fluidized bed, wherein the temperature of said fluidizing gas when introduced into said bed is sufficiently low such that the bed of tocopheryl succinate remains in a fluidized state during said contacting and said evaporating.

DETAILED DESCRIPTION OF THE INVENTION

This invention relates to a method for enlarging the size of solid particles of tocopheryl succinate. The starting tocopheryl succinate is a solid material and at no point in this process of size enlargement is the tocopheryl succinate melted. The product of the process are, in a sense, granules of tocopheryl succinate and binder because the process can be characterized as a granulation process. The term "granules" does not, however, denote a particular particle size, unless otherwise expressly noted herein. The product can also be considered a "coated" product in that the binder coats at least a portion of the surface of at least a portion of the tocopheryl succinate particles treated by the process.

In typical embodiments, the process can be characterized as spray-coating of powdered tocopheryl succinate (e.g. at least about 95 percent by weight of which is capable of passing through an 80-mesh (U.S. standard) sieve) with a solution containing a binder, typically in an amount corresponding to about 0.5 to about 15 percent by weight of binder solids based on the whole granular product weight (dried basis), while maintaining said powdered tocopheryl succinate in a fluidized state in a fluidized-bed granulation apparatus. The tocopheryl succinate to be used in the practice of the invention is typically in the free acid form. However, pharmaceutically acceptable salts, e.g. the sodium or potassium salts may also be useful.

The tocopheryl succinate used in this invention is initially in the form of a powder. This term, without further express limitation, denotes only that the product is of a size suitable for fluidization. The tocopheryl succinate typically consists essentially of particles having a relatively small average particle size, e.g. an average particle size of less than about 1 millimeter. Typically, the tocopheryl succinate will have essentially no particles (i.e. at most a trace amount) incapable of passing through an 80-mesh (U.S. standard) sieve (i.e. having openings of 180 micrometers).

The fluidized-bed granulation apparatus is a fluidized-bed drying apparatus equipped with one or more binder sprayers, in which granulation and drying can be carried out. Fluid bed granulators and granulation techniques are discussed in C. E. Capes, "Size Enlargement", *Encyclopedia of Chemical Technology*, vol. 21, pp. 77–105, (Kirk-Othmer, eds., John Wiley and Sons, Inc. NY.,N.Y., 1983), the disclosure of which is incorporated by reference. Fluidization phenomena are discussed in F. Zenz, "Fluidization", *Encyclopedia of Chemical Technology*, vol. 10, pp. 548–581 (Kirk-Othmer, eds., John Wiley and Sons, Inc. NY.,N.Y., 1980), the disclosure of which is incorporated by reference.

Typically, a fluid-bed granulator is a vessel having as a floor a perforated plate. Powdered feed is introduced above the plate while a gas, typically air, is blown from below the plate or drawn from the vessel above the plate such that the air passes through a bed of the feed material. The perforations are designed in conjunction with the air flow through the plate so as to fluidize the bed of feed material. A conduit typically conveys binder solution to a nozzle system suspended above the bed and binder solution passes through the nozzle system into the bed at a controlled rate.

As examples of such apparatus, there may be mentioned models available on the market under the names Glatt (made by Glatt AG in Germany), Aeromatic (made by Aeromatic AG in Switzerland), Calmic (made by Calmic Engineering Co. in Great Britain), Growmax (made by Fuji Powdal Co. in Japan), Flowcoater (Freund Industries Co. in Japan), and Gubler (made by Deseret Laboratories, Utah). An example of this latter apparatus is the Gubler 300 model. In this particular model, the particle size of product is influenced by the spacing of the spray head from the bed, the rate of spray of binder into the bed and the amount of binder as a percentage of the product on a dry basis. Thus, reducing the distance from the spray head to the bed, increasing the rate of spray of binder into the bed, and increasing the amount of binder in the product all tend to promote the formation of a product having a larger particle size. Conversely, increasing the distance from the spray head to the bed, reducing the rate of spray of binder into the bed, and reducing the amount of binder in the product all tend to inhibit the formation of a product having a larger particle size.

The binder to be contained in the solution for spray-coating can be a water-soluble binder or an organic solvent-soluble binder, depending on the choice of solvent. Because organic solvents have to be recovered for environmental reasons and because many organic solvents present an explosion hazard, water is typically employed as the sole solvent.

Examples of water-soluble binders include water-soluble celluloses, pregelatinized starches, and water-soluble macromolecules. The water-soluble celluloses include hydroxypropylcellulose, hydroxymethylcellulose, hydroxypropylmethylcellulose, carboxymethylcellulose and methylcellulose. Cellulose ethers are discussed in E. K. Just and T. G. Majewicz, "Cellulose Ethers", *Encyclopedia of Polymer Science and Engineering*, vol. 3, pp. 226–269 (John Wiley and Sons, Inc. NY.,N.Y., 1985) the disclosure of which is incorporated by reference. A preferred binder is hydroxypropylmethylcellulose (HPMC) and is available commercially from Dow Chemical Company, Midland, Mich. Some premium grades of HPMC which meet the requirement of U.S.P. XXIII and Food Chemicals Codex III are available.

A pregelatinized starch is a product obtained, for example, by heating a dispersion of starch in water, followed, as desired, by drying. Examples of the pregelatinized starches are pregelatinized corn starch, pregelatinized potato starch and pregelatinized modified starches (e.g. those described in the Code of Federal Regulations (U.S.A.), Title 21, Section 121.1031, Paragraphs a, b, c, d, e, f, g and h). There may also be used those pregelatinized and dried starches which are commercially available under the trademarks Amicol C (manufactured by Nichiden Chemical Co. in Japan), Pre-Gel (manufactured by Hubinger Co. in U.S.A.), Instant Cleargel (manufactured by National Starch Co. in U.S.A.), etc. Examples of water-soluble macromolecules includes polyvinylpyrrolidone (e.g. M.W. 10,000–100,000), polyvinyl alcohol (e.g. M.W. 10,000–50,000), dextrin, gum arabic, gum acacia, and gelatin.

Examples of organic solvent-soluble binders include, for example, an organic solvent-soluble cellulose derivative (e.g. cellulose acetate phthalate, hydroxypropylmethylcellulose phthalate, ethylcellulose). Among the various binders, water-soluble binders, especially water-soluble celluloses are preferably used.

As the solvent for dissolving the binder in preparing a binder solution for spraying, there may be mentioned solvents capable of dissolving the above-mentioned binders, such as water and, as organic solvent, alcohols (e.g. methyl alcohol, ethyl alcohol, isopropyl alcohol) and ketones (e.g. acetone).

The binder concentration is, for example, typically a concentration of about 1 to 20 percent by weight, more typically from about 5 to about 15 percent, and even more typically from about 8 to about 12 percent, by weight of the binder solution. The practical concentration varies with the binder-solvent combination employed, but is favorably such as to give a viscosity of about 1 to about 1,000 centipoise, preferably about 10 to about 500 centipoise which is typical for spraying. The granulation is carried out by spray-coating tocopheryl succinate powder with a solution containing a binder, while allowing the powder to be fluidized in a fluidized-bed granulation apparatus until the amount of the binder has reached that necessary to achieve the precise particle size desired, typically about 0.5 to 15%, and more typically from about 2 to about 10%, and even more typically from about 4 to about 8%, by weight relative to the weight of the granules. The solution of binder will typically be applied to the bed at a rate of about 0.01 to about 1.0 parts by weight of binder solution (on a basis of one hundred parts by weight of tocopherol succinate in the bed) per minute, more typically at a rate of about 0.2 to about 0.4 parts by weight of binder solution (on a basis of one hundred parts by weight of tocopherol succinate in the bed) per minute.

To allow the powder to dry, fluidizing gas, e.g. air, is continuously introduced. Other useful gases include inert gases, e.g. nitrogen. The use of heated gases to fluidize the bed, e.g. air above about 30° C., is to be avoided because elevation of the temperature of the bed results in a material that is not susceptible to fluidization. While the melting point of the tocopheryl succinate is about 72° C. to 75° C., it has been found that the use of heated air causes the particles to de-fluidize, typically coalescing into a mass that cannot be handled in the fluid-bed granulator. Typically, the temperature of the gas introduced into the bed will be between about 0° C. to about 25° C. Even more typically, the temperature of said fluidizing gas upon contact with said bed during said contacting will be less than about 20° C., but the temperature of said fluidizing gas is then increased after said contacting to a temperature greater than about 20° C. To maintain an appropriate bed temperature, it is convenient to monitor the outlet temperature to ensure that the outlet temperature does not exceed 30° C. If the outlet temperature approaches 30° C., the inlet temperature of the fluidizing gas should be lowered.

Of course, the gas used to fluidize the bed during the evaporation phase of the process should not be saturated in the solvent to be evaporated. Nor should a gas that is too dry be used, particularly in the contacting phase of the process because uneven drying in the bed, should not be used. Typically, it is useful to dehumidify the air that is to be introduced into the bed and then rehumidify it to the desired low humidity.

After granulation and evaporation of solvent, typically to less than 4%, more typically not more than 3%, and preferably essentially to dryness, e.g. not more than 2% moisture, the granules of tocopheryl succinate and binder are removed from the fluid-bed granulator. The product should be maintained in a fluidized state until the desired degree of evaporation has been obtained. Because attrition of the product also occurs in the fluidized bed, the product should be removed from the bed once the desired degree of evaporation is obtained. The process can be accomplished in a batch or continuous mode. Because of the long cycle time that may be necessary to achieve complete drying without heat, a batch process will typically be used.

The product can be characterized as a granular composition. If desired, it can be sieved and/or passed through a mill, such as a Power mill or a Fitz mill, in order to crush some aggregates to get a more precise grain size distribution.

The method of this invention produces granules which consist essentially of tocopheryl succinate and a binder, with the tocopheryl succinate typically accounting for about 85 to about 99.5%, more typically from 92 to about 96%, by weight on a dried basis. A lower limit on grain size is typically a maximum of 5% by weight of the grains through a 120-mesh sieve. In certain embodiments, the product will have a relatively smaller grain size than in other embodiments, e.g. a minimum of 95% through a 20-mesh sieve and a maximum of 5% by weight of the grains through a 120-mesh sieve. In these embodiments, an average particle size of about 80-mesh would be typical. In other embodiments, the grain size is such that the portion of grains on a 20-mesh sieve is a minimum of 30%, more typically 35% and that portion which passes through an 80-mesh sieve accounts for not more than 5%, more typically 10%, by weight. An excessively fine composition is also undesirable because of its poor flowability in charging into dies in tabletting. In general, this relatively larger grain product will also typically have that portion of grains which does not pass through a 10-mesh (U.S. standard) sieve account for not more than a trace, e.g. less than 1% by weight. An excessively coarse granular composition is unsuited for admixture with some other granular composition and moreover causes weight fluctuation in tablet manufacture.

The tocopheryl succinate granules according to the invention can be used as a raw material in the manufacture of tocopheryl succinate-containing tablets and capsules.

Tabletting of the granules is carried out by a conventional method in the presence of a lubricant and, if necessary, some other drug substance and/or an excipient (e.g. lactose, sucrose, mannitol). As said lubricant, there may be mentioned those lubricants which are used in conventional tablet manufacture, such as stearic acid and stearates (e.g. magnesium stearate, calcium stearate) and talc. The amount and kind of the lubricant are selected within such a range as to give tablets which are practical from the strength and disintegration viewpoint. Typically, it is used in an amount of about 0.1 to about 7 percent by weight based on the main active substance. Of the lubricants, a stearate or stearic acid is typically added in an amount of at least about 0.5 percent by weight based on the main active substance. The above-mentioned other drug substance can include a variety of vitamins, mineral, and other dietary supplements. The compression is normally carried out under the condition of 1 to 2 ton/cm$^2$.

In accordance with the method of the invention, there can be obtained tocopheryl succinate granules of tocopheryl succinate powder uniformly coated with a small amount of a binder. The granules can be compressed into tablets containing the high concentration of tocopheryl succinate only by a simple procedure comprising mixing the granules with a lubricant and other ingredients and tabletting the mixture. The granules do not contain fine powder and have good flowability. These characteristics are favorable as a raw material for direct compression, and also convenient for handling, and scarcely lead to dust rising. The granules are suited for the manufacture of multivitamin preparations. The hardness of the whole tablet can be secured by the use of the granules with good bonding properties.

The mesh sizes as defined in this specification are those specified in the relevant U.S. standard (as published in *Handbook of Chemistry and Physics*, p. F-158 (57 th ed., CRC Press, Cleveland Ohio, 1976)). Said mesh sizes and the corresponding sieve opening sizes are shown below.

| Mesh | Sieve opening size (micrometers) |
|---|---|
| 10 | 2,000 |
| 20 | 850 |
| 80 | 180 |
| 120 | 125 |

The following examples will illustrate the invention and should not be construed to limit the invention, except as expressly noted in the appended claims. All parts, ratios and percentages are by weight unless noted otherwise in context.

EXAMPLES

Example 1

A fluidized-bed granulation apparatus (Gubler model 300, Deseret Laboratories, St. George, Utah) is charged with 250 parts of tocopheryl succinate powder (available from Henkel Corp., Ambler, Pa., as Covitol 1210). The powder is fluidized with air at an inlet temperature of 0° C. and with a maximum setting for the outlet temperature of 30° C. The bed is sprayed with a solution of 10.5 parts of hydroxypropylmethylcellulose (available from Dow Chemical Company, Midland, Mich., as Methocel E-5, premium grade) in 94.6 parts of water which is prepared in advance by dispersing the HPMC in water to make a concentration of about 10% by weight followed by standing for about one hour to degas. The rate of spray is about 0.5 to 1 part per minute. The spraying is stopped when the amount of the solids of HPMC binder sprayed reaches an amount corresponding to about 10% of the solids in the bed. After spraying is completed, fluidization of the bed is continued with a slow gradual increase in the inlet temperature to 25° C. The moisture of the product in the bed is tested periodically. When the moisture falls to 3% by weight, fluidization is stopped and the product is removed from the bed.

Example 2

The procedures of Example 1 were followed except spraying is stopped when the amount of solids of HPMC binder sprayed reaches 8% of the solids in the bed.

Example 3

The procedures of Example 1 were followed except spraying is stopped when the amount of solids of HPMC binder sprayed reaches 6% of the solids in the bed.

Example 4

The procedures of Example 1 were followed except spraying is stopped when the amount of solids of HPMC binder sprayed reaches 4% of the solids in the bed.

Example 5

The procedures of Example 1 were followed except spraying is stopped when the amount of solids of HPMC binder sprayed reaches 2% of the solids in the bed.

Example 6

The procedures of Example 1 were followed except spraying is stopped when the amount of solids of HPMC binder sprayed reaches 1% of the solids in the bed.

Example 7

The procedures of Example 1 were followed except spraying is stopped when the amount of solids of HPMC binder sprayed reaches 0.5% of the solids in the bed.

What is claimed is:

1. A process of producing a coated tocopheryl succinate comprising
   contacting a tocopheryl succinate powder with a solution of a pharmaceutically acceptable binder, said tocopheryl succinate being maintained in a fluidized stare during said contacting by passage of a fluidizing gas through a bed of the tocopheryl powder; and
   evaporating solvent from said contacted tocopheryl succinate in said fluidized bed, wherein the temperature of said fluidizing gas when introduced into said bed is sufficiently low such that the bed of tocopheryl succinate remains in a fluidized state during said contacting and said evaporating.

2. The process as claimed in claim 1 wherein the temperature of said fluidizing gas after contact with said bed during the evaporation is not more than about 30° C.

3. The process as claimed in claim 1 wherein said tocopheryl succinate powder has an average particle size of less than about 1 millimeter.

4. The process as claimed in claim 1 wherein said tocopheryl succinate powder contains essentially no particles incapable of passing a sieve having openings of 180 micrometers.

5. The process as claimed in claim 1 wherein said tocopheryl succinate powder consists essentially of the free acid form of tocopheryl succinate.

6. The process as claimed in claim 1 wherein said binder is a water-soluble cellulose.

7. The process as claimed in claim 1 wherein said binder is a water-soluble cellulose selected from the group consisting of hydroxypropylcellulose, hydroxymethylcellulose, hydroxypropylmethylcellulose, carboxymethylcellulose, and methylcellulose.

8. The process as claimed in claim 1 wherein the solvent of said solution consists essentially of water.

9. The process as claimed in claim 1 wherein said fluidized bed is present above a perforated plate through which said gas is passed at a rate sufficient to maintain the bed in a fluidized state.

10. The process as claimed in claim 1 wherein said fluidizing gas is air.

11. The process as claimed in claim 1 wherein said fluidizing gas consists essentially of nitrogen.

12. The process as claimed in claim 1 wherein said contacting is accomplished by spraying said bed with said solution.

13. The process as claimed in claim 1 wherein the amount of said binder is from about 0.5% to about 15% by weight of said tocopheryl succinate powder.

14. The process as claimed in claim 1 wherein the amount of said binder is from about 2% to about 10% by weight of said tocopheryl succinate powder.

15. The process as claimed in claim 1 wherein the amount of said binder is from about 4% to about 8% by weight of said tocopheryl succinate powder.

16. The process as claimed in claim 1 wherein said binder is hydroxypropylmethylcellulose.

17. The process as claimed in claim 1 wherein the concentration of said binder in said solution is from about 1% to 20% by weight of the binder solution.

18. The process as claimed in claim 1 wherein the concentration of said binder in said solution is from about 5% to about 15% by weight of the binder solution.

19. The process as claimed in claim 1 wherein the concentration of said binder in said solution is from about 8% to about 12% by weight of the binder solution.

20. The process as claimed in claim 1 wherein the temperature of said fluidizing gas upon contact with said bed during said contacting is less than about 20° C.

21. The process as claimed in claim 20 wherein the temperature of said fluidizing gas is increased after said contacting to a temperature greater than about 20° C.

22. The process as claimed in claim 1 wherein the solvent of said binder solution is water and said evaporating is effective to reduce the moisture of said bed to less than 4% by weight.

23. The process as claimed in claim 1 wherein the solvent of said binder solution is water and said evaporating is effective to reduce the moisture of said bed to not more than 3% by weight.

24. The process as claimed in claim 1 wherein the solvent of said binder solution is water and said evaporating is effective to reduce the moisture of said bed to not more than 2% by weight.

25. The process as claimed in claim 1 wherein the process is accomplished in a batch mode.

26. The process as claimed in claim 1 wherein the particle size of the tocopheryl succinate recovered from said bed after said evaporating is such that maximum of 5% by weight will pass through a sieve having openings of 125 micrometers.

27. The process as claimed in claim 1 wherein the particle size of the tocopheryl succinate recovered from said bed after said evaporating is such that minimum of 35% by weight will be retained on a sieve having openings of 850 micrometers.

28. The process as claimed in claim 1 wherein the particle size of the tocopheryl succinate recovered from said bed after said evaporating is such that maximum of 10% by weight will pass through a sieve having openings of 180 micrometers.

29. The process as claimed in claim 1 wherein the particle size of the tocopheryl succinate recovered from said bed after said evaporating is such that maximum of 5% by weight will pass through a sieve having openings of 180 micrometers.

30. A process of producing a coated tocopheryl succinate comprising:

contacting a material consisting essentially of tocopheryl succinate powder having an average particle size of less than about 180 micrometers with a solution consisting essentially of a water-soluble cellulose and water, said tocopheryl succinate being maintained in a fluidized bed during said contacting by passage of air through said bed, evaporating water from said contacted tocopheryl succinate in said fluidized bed, wherein the temperature of said fluidizing gas when introduced into said bed is maintained below about 30° C., and recovering from said bed a tocopheryl succinate product wherein the particle size of the tocopheryl succinate recovered from said bed after said evaporating is such that maximum of 5% by weight will pass through a sieve having openings of about 125 micrometers.

31. The process as claimed in claim 30 wherein said water-soluble cellulose is hydroxypropylmethylcellulose.

32. The process as claimed in claim 31 wherein the amount of said binder is from about 4% to about 8% by weight of said tocopheryl succinate powder.

33. The process as claimed in claim 32 wherein said evaporating is effective to reduce the moisture of said tocopheryl succinate product to less than about 4%.

34. The process as claimed in claim 33 wherein the particle size of the tocopheryl succinate recovered from said bed after said evaporating is such that maximum of 10% by weight will pass through a sieve having openings of about 180 micrometers.

35. A process as claimed in claim 1 wherein the temperature of said fluidizing gas upon contact with said bed is between about 0° to about 25° C.

* * * * *